United States Patent
Chen et al.

(10) Patent No.: US 8,232,408 B2
(45) Date of Patent: Jul. 31, 2012

(54) CRYSTALLINE 1-(3-FLUOROPHENYL)-5-METHYL-2-(1H)PYRIDONE, THE PREPARATION METHODS, COMPOSITIONS AND APPLICATIONS THEREOF

(75) Inventors: Jiamei Chen, Dongguan (CN); Tongbu Lu, Dongguan (CN); Song Chen, Dongguan (CN); Jinghui Cai, Dongguan (CN); Zhaolin Fu, Dongguan (CN); Zhe He, Dongguan (CN); Xuefeng Wang, Dongguan (CN); Chaozhi Wang, Dongguan (CN); Yonge Liu, Dongguan (CN); Lijian Tao, Dongguan (CN); Gaoyun Hu, Dongguan (CN)

(73) Assignee: Sunshine Lake Pharma Co., Ltd., Dongyangguang Hi-tech Park, Shang Sha, Chang An Town, Dongguan, Guangdong (CN)

( * ) Notice: Subject to any disclaimer, the term of this patent is extended or adjusted under 35 U.S.C. 154(b) by 127 days.

(21) Appl. No.: 12/920,320

(22) PCT Filed: Mar. 10, 2009

(86) PCT No.: PCT/CN2009/000256
§ 371 (c)(1),
(2), (4) Date: Aug. 31, 2010

(87) PCT Pub. No.: WO2009/111947
PCT Pub. Date: Sep. 17, 2009

(65) Prior Publication Data
US 2011/0003864 A1 Jan. 6, 2011

(30) Foreign Application Priority Data
Mar. 10, 2008 (CN) .......................... 2008 1 0101643

(51) Int. Cl.
*C07D 211/72* (2006.01)
*A61K 31/44* (2006.01)
(52) U.S. Cl. ........................................ 546/290; 514/345
(58) Field of Classification Search .................. None
See application file for complete search history.

(56) References Cited

U.S. PATENT DOCUMENTS
2007/0203203 A1    8/2007    Tao et al.

FOREIGN PATENT DOCUMENTS
| CN | 1386737 | 12/2002 |
| EP | 1878428 | 1/2008 |
| WO | WO2008/131586 | 11/2008 |

OTHER PUBLICATIONS

Bhattacharya, S. et al excerpt from Brittain, Polymorphism in Pharmaceuticcal Solids, Informa Healthcare 2009, pp. 318-334.*
Extended EP Search Report, Apr. 21, 2011.

* cited by examiner

*Primary Examiner* — Janet Andres
*Assistant Examiner* — Heidi Reese
(74) *Attorney, Agent, or Firm* — Kam W. Law; Squire Sanders (57) ABSTRACT

Crystalline pyridone compound, which is the white needle crystal containing no water and other crystallization solvents. Its unit cell belongs to monoclinic system and has space group of $P2_1/n$, wherein a=3.8512(2), b=20.2535(12), c=12.1628(6) Å, β=92.850(5)° and crystal cell volume V=947.53(9) Å$^3$. Pyridone compound crystal of this form has the needed properties for preparing or making treatment compositions in large scale. It can be used for treating organs fibrosis of liver, kidney, lung and etc. and reducing skin scars.

25 Claims, 3 Drawing Sheets

CRYSTALLINE 1-(3-FLUOROPHENYL)-5-METHYL-2-(1H)PYRIDONE, THE PREPARATION METHODS, COMPOSITIONS AND APPLICATIONS THEREOF

PRIOR RELATED APPLICATIONS

This is a U.S. national stage application of the International Patent Application No. PCT/CN2009/000256, filed Mar. 10, 2009, which claims priority to Chinese Patent Application No. 200810101643.X, filed Mar. 10, 2008, both of which are incorporated herein by reference in their entirety.

FIELD OF THE INVENTION

This invention relates to a crystalline pyridone compound 1-(3-fluorophenyl)-5 methyl-2-(1H)-pyridone (Flurofenidone, or known as "FFD"), the preparation and application thereof.

BACKGROUND OF THE INVENTION

The Chinese Patent Application ZL 02114190.8 discloses 1-(substituted phenyl)-5-methyl-2-(1H)-pyridone compounds, wherein one of the compounds is FFD when n is 1, R is F and the R substituent is at the meta-position of the phenyl group. It also discloses the method for preparing 1-(substituted phenyl)-5-methyl-2-(1H)-pyridone compounds, but it does not disclose crystallization and purification methods for FFD. According to the method disclosed in the Chinese patent application, highly pure crystalline FFD cannot be obtained.

A cell experiment testing the effect of FFD on anti-fibrosis of renal interstitial cell is disclosed in the Journal of Central South University (Medical Sciences), 2004, vol. 29 (2), the result shows that FFD has a good effect on anti-fibrosis.

It is disclosed in the CN 1846699A and US20070203203 that FFD is useful for preventing and treating tissue and organ fibrosis of animal and human.

To date, there is no report about preparation of the crystalline FFD.

Methods for crystallizing organic compounds have been reported in the following documents: J. A. Landgrebe, *Theory and Practice in the Organic Laboratory*, $2^{nd}$ Edition, pp. 43-51, published by D.C. Health and Co., Lexington (1977); and A. S. Myerson, *Handbook of Industrial Crystallization*, pp. 1-101, published by Butterworth Heinemann, Stoneham (1933).

DETAILED DESCRIPTION OF THE INVENTION

One objective of the present invention is to provide a crystalline pyridone compound 1-(3-fluorophenyl)-5-methyl-2-(1H)-pyridone (Flurofenidone, or known as "FFD"). Pyridone compound crystals of this form have the needed properties for preparing or making treatment compositions in large scale.

Another objective of the present invention is to provide a method for preparing the crystalline FFD compound.

Another objective of the present invention is to provide a composition comprising the crystalline FFD compound.

Another objective of the present invention is to provide the preparation and application of the compositions comprising the crystalline FFD compound for treating organs fibrosis of liver, kidney, lung and the like and for reducing skin scar.

Figure 1:
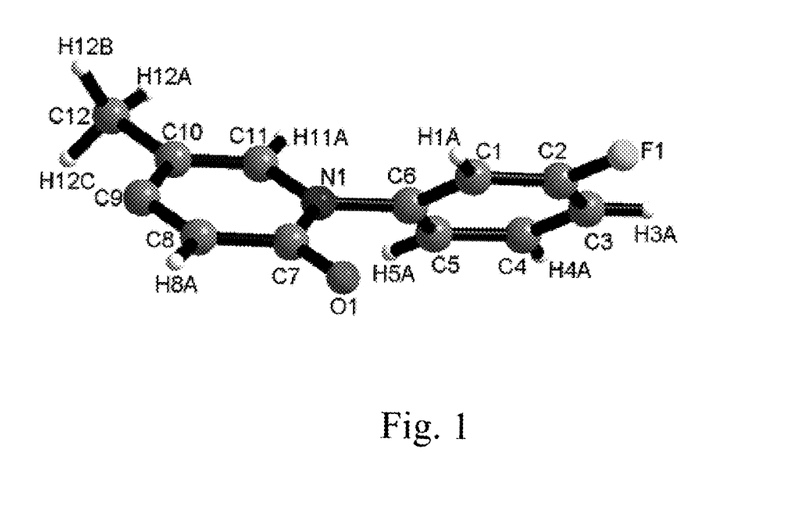
FIG. 1 depicts the single-crystal structure of the crystalline FFD of the invention.
Figure 2:
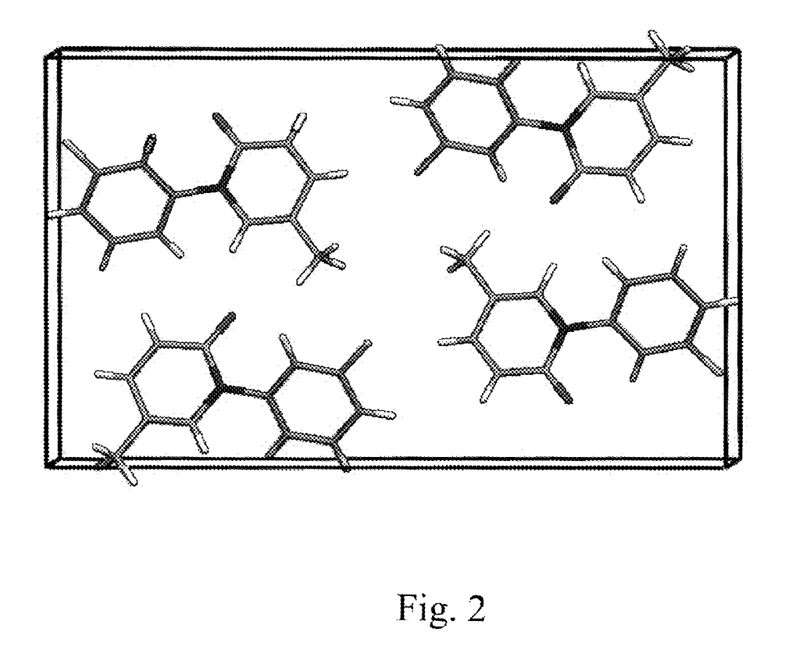
FIG. 2 depicts the unit cell of the crystalline FFD of the invention.

In order to achieve the objectives of the present invention, the crystalline pyridone compound 1-(3-fluorophenyl)-5-methyl-2-(1H)-pyridone (Flurofenidone, or known as "FFD") is characterized as being a white needle shaped crystal containing no water or other solvents of crystallization. Its unit cell belongs to monoclinic system, and has a space group of $P2_1/n$, wherein a=3.8512(2), b=20.2535(12), c=12.1628(6) Å, β=92.850(5)°, and crystal cell volume V=947.53(9) Å$^3$. X-ray diffraction patterns of a single-crystal of the crystalline FFD are shown in FIG. 1, and its unit cell is shown in FIG. 2.

The crystalline FFD of the invention is characterized by using Cu-Ka radiation. The X-ray diffraction pattern shown in FIG. 3 comprises peaks expressed in degrees 2θ at 8.7, 11.2, 14.4, 15.1, 17.4, 18.9, 19.5, 22.7, 23.9, 25.5, 26.3, 26.7, 27.3, 27.8, 28.8, 29.6, 30.5, 33.4, 34.3, 36.1, 39.2, 40.6, 42.6, 44.6, 45.2, 47.1.

Figure 4:
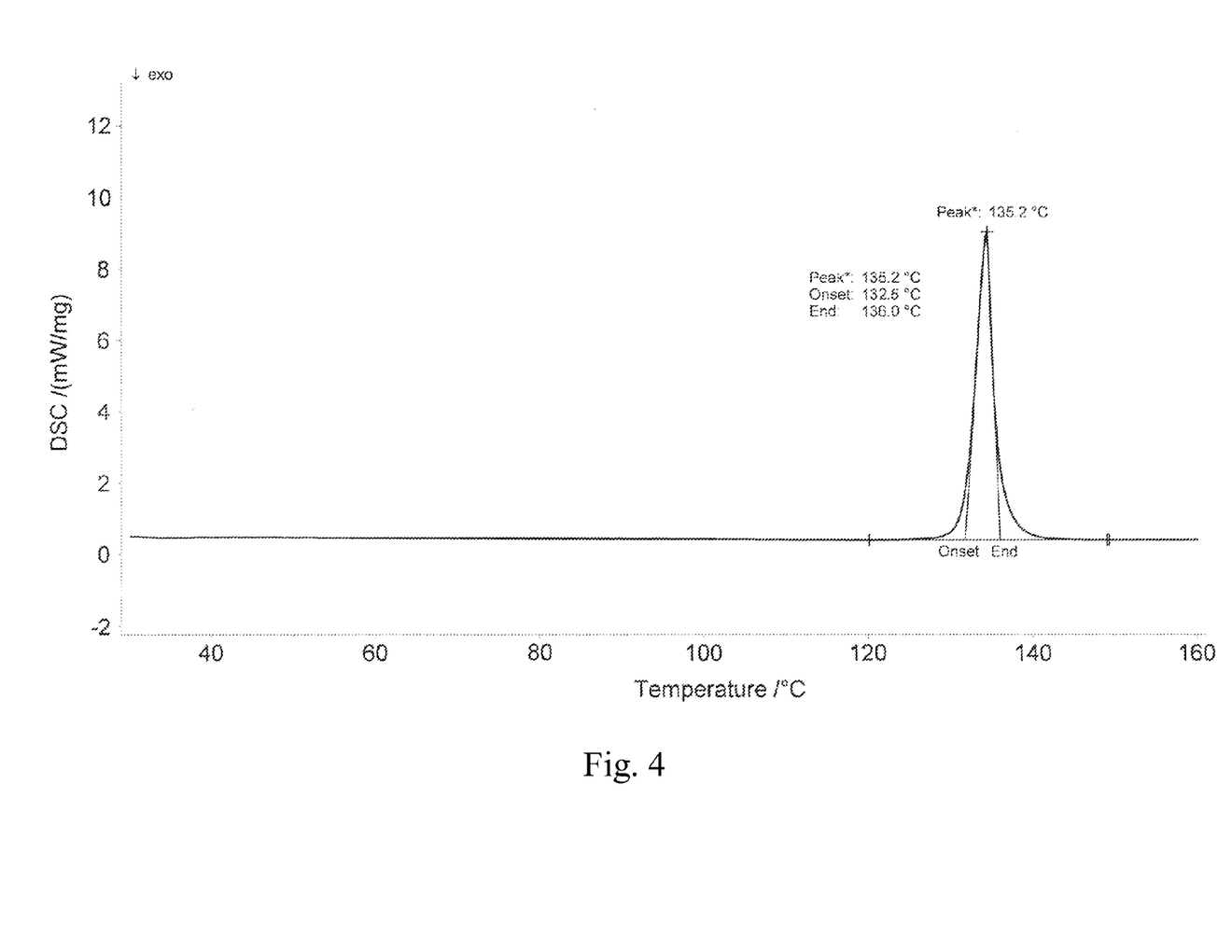
FIG. 4 depicts the differential scanning calorimetry (DSC) curve of the crystalline FFD of the invention.

The differential scanning calorimetry (DSC) curve of the crystalline FFD of the invention is shown in FIG. 4 and its endothermic transition temperature is 135.2° C.

Diffraction experiments done on the crystalline FFD of the present invention are performed on a Bruker SMART 1000 CCD single-crystal X-ray diffractometer with graphite monochromator at 150 (2) K. MoKα (0.071073 nm) radiation is used and data are collected by ω/2θ scan mode. The data are processed with a SAINT+ program package and are corrected for absorption effects by using a SADABS program. The space group is determined by the system extinction rule and confirmed by refinement results. All crystal structures are solved with direct methods using full matrix least-squares refinement of a SHELXS-97 program. Hydrogen atoms are placed in theoretical calculated positions.

The method for preparing the crystalline FFD of the invention comprises the following steps of:

dissolving 1-(3-fluorophenyl)-5-methyl-2-(1H)-pyridone in an organic solvent first; and forming the white needle shaped crystalline 1-(3-fluorophenyl)-5-methyl-2-(1H)-pyridone after the evaporation of the organic solvent while kept still. The yield is more than 85%.

The solubility of FFD significantly increases from 1.41-1.49 mg/ml (25±1° C.) to 2.44~2.55 mg/ml (25±1° C.) after crystallization. (Testing method is according to the "Testing Method For Determining The Solubility" in The Chinese Pharmacopoeia 2005, the example section of the second part, the last line on the first page to the first line on the second.)

The organic solvent is ethyl acetate, methanol, ethanol, acetone or the like.

The crystalline FFD of the invention has the needed properties for preparing or making treatment compositions in large scale. The crystalline FFD of the invention also has a good melting point, good flowability and bulk density, rendering it easier to prepare and manufacture the compositions containing the crystalline FFD. The present invention can eliminate or minimize by-products generated during the synthetic process of making FFD so as to produce highly pure FFD having a purity of at least about 98% (w/w). Therefore, costly and time-consuming column chromatography purification of FFD can be avoided. Furthermore, the crystalline FFD of the invention is a form of FFD having a long storage-life.

The present invention can be used to prepare into the crystalline FFD solid dispersion to further improve the water solubility of the crystalline FFD; to render the product having a high efficacy and good uniformity; and to ensure the final composition having a high bioavailability.

The crystalline FFD solid dispersion of the invention comprises the crystalline FFD, a solubilizer and a polymer base material, wherein their ratio by weight is 1:0.1-0.5:4-10.

The solubilizer is sodium dodecyl sulphate, vitamin C, tween-20, tween-21, tween-40, tween-60, tween-61, tween-65, tween-80, tween-81, tween-85, tween-120, myrij, brij, poloxamer, caprylic/capric glyceride (PEG-8), lithium polyethylene glycol 12-hydroxystearate, polyoxyethylene stearic acid ester, polyoxyethylene castor oil, polyoxyethylene hydrogenated castor oil or lecithin.

The polymer base material is polyethylene glycol (PEG4000, PEG6000), xanthan gum, PEG12000, PEG20000, PVPK90, PVP10000, PVP40000 or poloxamer 188.

In order to further increase the solubility of the crystalline FFD, a co-solvent such as ethanol, glycol, propylene glycol or glycerol, which presents in an amount of 0.1-0.5 times by weight relative to the weight of the crystalline FFD, can be added.

The method for preparing the crystalline FFD solid dispersion of the invention, comprises the following steps of:

heating the polymer base material to a melt (preferably 80-120° C.) first; then mixing the crystalline FFD with the solubilizer; adding the mixture into the polymer base material; solidifying the mixture by rapid cooling (preferably within 5-20 minutes) to 20-35° C.; and finally freeze-drying the mixture into a powder.

In order to dissolve and disperse the crystalline FFD more easily, the co-solvent can be added in proportion when the crystalline FFD is mixing with the solubilizer.

The crystalline FFD solid dispersion of the invention is obtained from the surface of the polymer base material to which the crystalline FFD particles attach. Precipitating the active pharmaceutical ingredients onto the base material is for minimizing aggregation between the active pharmaceutical ingredients and the base material particles, which can improve the dissolution rate and the solubility of the crystalline FFD, which in turn may improve the absorption and bioavailability of the medicament.

The crystalline FFD solid dispersion of the invention can be used to prepare any dosage form for any suitable administration method, such as oral administration in the form of tablets, capsules, granules or powders. It can be prepared by mixing the crystalline FFD solid dispersion with disintegrants, glidants, lubricants, suspending agents and adhesives and then pressing the powder into tablets, filling into capsules, or making into granules. According to the any method known in this technical field, the crystalline FFD pharmaceutical composition can also be prepared for non-gastrointestinal, rectal, nasal administrations and the like. This kind of composition can comprises excipients which include commonly used diluents, gilants, lubricants, disintegrants, adhesives, suspension agents and the like. The present invention also includes sustained-release and controlled-release compositions.

Certainly, the crystalline FFD of the invention can also be prepared into various kinds of pharmaceutical compositions with other active pharmaceutical ingredients.

The crystalline FFD of the invention is prepared into solid dosage forms, such as capsules or tablets, comprising the ingredients and their weight percentages as stated below:

| Crystalline FFD solid dispersion | 1-80%, |
|---|---|
| adhesive | 1-10%, |
| diluent | 10-80%, |
| lubricant | 1-5%, |
| disintegrant | 1-8%. |

The adhesive is povidone, methyl cellulose, hydroxyl methyl cellulose, hydroxyl propyl methyl cellulose, hydroxyl propyl cellulose or hydroxyl ethyl cellulose. Povidone and hydroxyl methyl cellulose are preferred.

The diluent is lactose, xylitol, microcrystalline cellulose, dextrin, mannitol, sorbitol, sucrose, starch, pregelatine starch, glucose, calcium phosphate, dicalcium phosphate, calcium carbonate, or a mixture thereof.

The lubricant is siliciidoxydum, magnesium stearate, stearic acid, sodium octadecyl fumarate or sodium dodecyl sulfate. Siliciidoxydum and magnesium stearate are preferred.

The disintegrant is polyvinylpyrrolidone, croscarmellose, low-substituted hydroxyl propylmethylcellulose, sodium carboxy methyl starch medicinal, pregelatine starch or corn starch. Polyvinylpyrrolidone is preferred.

When the crystalline FFD is prepared into granules, the composition comprises ingredients and their weight percentages as stated below:

| Crystalline FFD solid dispersion | 1-80%, |
|---|---|
| adhesive | 1-10%, |
| diluent | 10-85%, |
| solubilizer | 1-6%, |
| preservative | 0.1-1%. |

The adhesive is povidone, methyl cellulose, hydroxyl methyl cellulose, hydroxyl propyl methyl cellulose, hydroxyl propyl cellulose or hydroxyl ethyl cellulose. Povidone and hydroxyl methyl cellulose are preferred.

The diluent is lactose, xylitol, microcrystalline cellulose, dextrin, mannitol, sorbitol, sucrose, starch, pregelatine starch, glucose, calcium phosphate, dicalcium phosphate, calcium carbonate or a mixture thereof.

The solubilizer is poloxamer, lecithin, vitamin C, tween-80, tween-60, tween-65, polyoxyethylene castor oil or the like. Poloxamer and tween-80 are preferred.

The preservative is p-hydroxy benzoate ester, benzoic acid, sodium benzoate, sorbic acid, benzalkonium bromide or the like. p-Hydroxy benzoate ester is preferred.

When the crystalline FFD is prepared into a suspension, the composition comprises ingredients and their weight percentages as stated below:

| Crystalline FFD solid dispersion | 1-80%, |
|---|---|
| suspending agent | 0.8-8%, |
| solubilizer | 0.5-6%, |
| flavoring agent | 0.1-50%, |
| preservative | 0.1-1%, |
| water | remaining amount. |

The suspending agent is CMC-Na, xanthan gum, methyl cellulose, sodium alginate, potassium alginate, HPMC, chitin, tragacanth, agar or the like. CMC-Na is preferred.

The solubilizer is poloxamer, lecithin, vitamin C, tween-80, tween-60, span-65, polyoxyethylene castor oil or the like. Poloxamer and tween-80 are preferred.

The flavoring agent is sucrose, aspartame, steviol glycosides, sodium saccharin or the like. Sucrose and steviol glycosides are preferred.

The preservative is p-hydroxy benzoate ester, benzoic acid, sodium benzoate, sorbic acid, benzalkonium bromide or the like. p-Hydroxy benzoic acid esters is preferred.

When the crystalline FFD is prepared into an emulsion, the composition comprises ingredients and their weight percentages as stated below:

| | |
|---|---|
| Crystalline FFD solid dispersion | 1-80%, |
| semi-solid material | 10-60%, |
| emulsifier | 1-10%, |
| suspending agent | 1-8%, |
| solvent | remaining amount. |

The semi-solid material is Vaseline, solid paraffin, liquid paraffin, ozocerite, peanut oil, castor oil, soybean oil, palm oil, cottonseed oil, silicone, lanolin, sodium laurel alcohol sulfate, hexadecanol, octadecanol, cellulose or the like. Vaseline, silicone, lanolin, PEG, carbomer are preferred.

The emulsifier is tragacanth, gelatin, phospholipid, almond, cholesterol, bletilla mucilage, pectin, agar, sodium alginate, methyl cellulose, sodium stearate, potassium stearate, calcium stearate, sodium oleate, potassium oleate, sorbitan fatty acid (20, 40, 60, 80, etc.), polysorbate (20, 40, 60, 80, etc.), aluminum hydroxide, calcium hydroxide or the like. Arabic gum, sorbitan fatty acid, polysorbate are preferred.

The suspending agent is CMC-Na, xanthan gum, methyl cellulose, sodium alginate, potassium alginate, HPMC, chitin, tragacanth, gelatin or the like. CMC-Na is preferred.

The solvent is water, ethanol or glycerol or glycol.

When the crystalline FFD is prepared into a semi-solid composition, the composition comprises ingredients and their weight percentages as stated below:

| | |
|---|---|
| Crystalline FFD solid dispersion | 1-80%, |
| semi-solid material | 10-60%, |
| solubilizer | 0.5-6%, |
| water | remaining amount. |

The semi-solid material is Vaseline, solid paraffin, liquid paraffin, ozocerite, peanut oil, castor oil, soybean oil, palm oil, cottonseed oil, silicone, lanolin, sodium laurel alcohol sulfate, hexadecanol, octadecanol, cellulose, or the like. Vaseline, silicone, lanolin, PEG, carbomer are preferred.

The solubilizer is poloxamer, lecithin, vitamin C, tween-80, tween-60, span-65, polyoxyethylene castor oil or the like. Poloxamer and tween-80 are preferred.

The crystalline FFD compositions of the invention can further comprise colorants which present in an amount of 0.0001-0.05% of the total weight, wherein the colorants are natural pigments, synthetic pigments or the like. The natural pigments are preferred.

The present invention provides the preparation and application of the composition comprising the crystalline FFD for treating organ fibrosis of liver, kidney, lung and the like, and for reducing skin scar.

Where the compositions disclosed in the present invention contain 3-3000 mg of the crystalline FFD, one to three times daily administration is recommended for treating fibrosis. The compositions preferably comprise about 3-300 mg of the crystalline FFD and more preferably 15-150 mg of the crystalline FFD. Both compositions are administrated one to three times daily for treating organ fibrosis.

The daily administration of the crystalline FFD compositions can also be used infrequently for some patients. For example, the patients, whose fibrosis has been controlled by taking the crystalline FFD composition daily, can avoid further infection by performing maintenance therapy. This maintenance therapy includes less than one administration of the crystalline FFD composition per week. For example, one administration every three or four days is enough.

In order to expand the treatment choice and make the treatment more convenient for patients, the dissolution of the oral administration crystalline FFD is improved. This ensures a relatively stable dissolving rate of drug in the patient body and therefore ensures a steady absorption rate of drug and a relatively stable bioavailability. Compared with the previous dosage forms such as the powder form, the crystallize FFD compositions of the invention has the following merits:

1. Because of electrostatic attraction, strong aggregation, large angles of repose and poor dispersion of the powder of the crystalline FFD, it is difficult to divide the powder of the crystalline FFD into doses. After the compositions are prepared from the powder, dividing the compositions into doses becomes accurate, and contact contamination is reduced in the manufacturing process, and the quality of product is better ensured.

2. The water solubility of the crystalline FFD is 2.44~2.55 mg/ml (25±1)° C., (Testing method is according to the "Testing Method For Determining The Solubility" in The Chinese Pharmacopoeia 2005, the example section of the second part, the last line on the first page to the first line on the second), which is still low due to high lipophilicity. The crystalline FFD compositions of the invention improve the lipophilicity to increase the water solubility significantly by 20-30 times. It can ensure that the drug can be steadily released after taking orally. The drug can mix with one's internal environment easily after release, which renders the steady absorption of the drug, and the achievement of a relatively stable bioavailability.

EXAMPLES

The following examples will further illustrate the present invention, but they should not be construed to unduly limit this invention.

Example 1

FFD white powder (0.4 g) was added into 10 mL ethyl acetate in a 25 mL test tube. The powder was dissolved with heating and stirring, and then cooled down. A transparent and clear solution was obtained. After the evaporation of ethyl acetate while standing at room temperature for about one week, a white needle shaped crystal (0.35 g) was formed. The purity (HPLC) was 99.1% and the yield was 88%.

Figure 3:
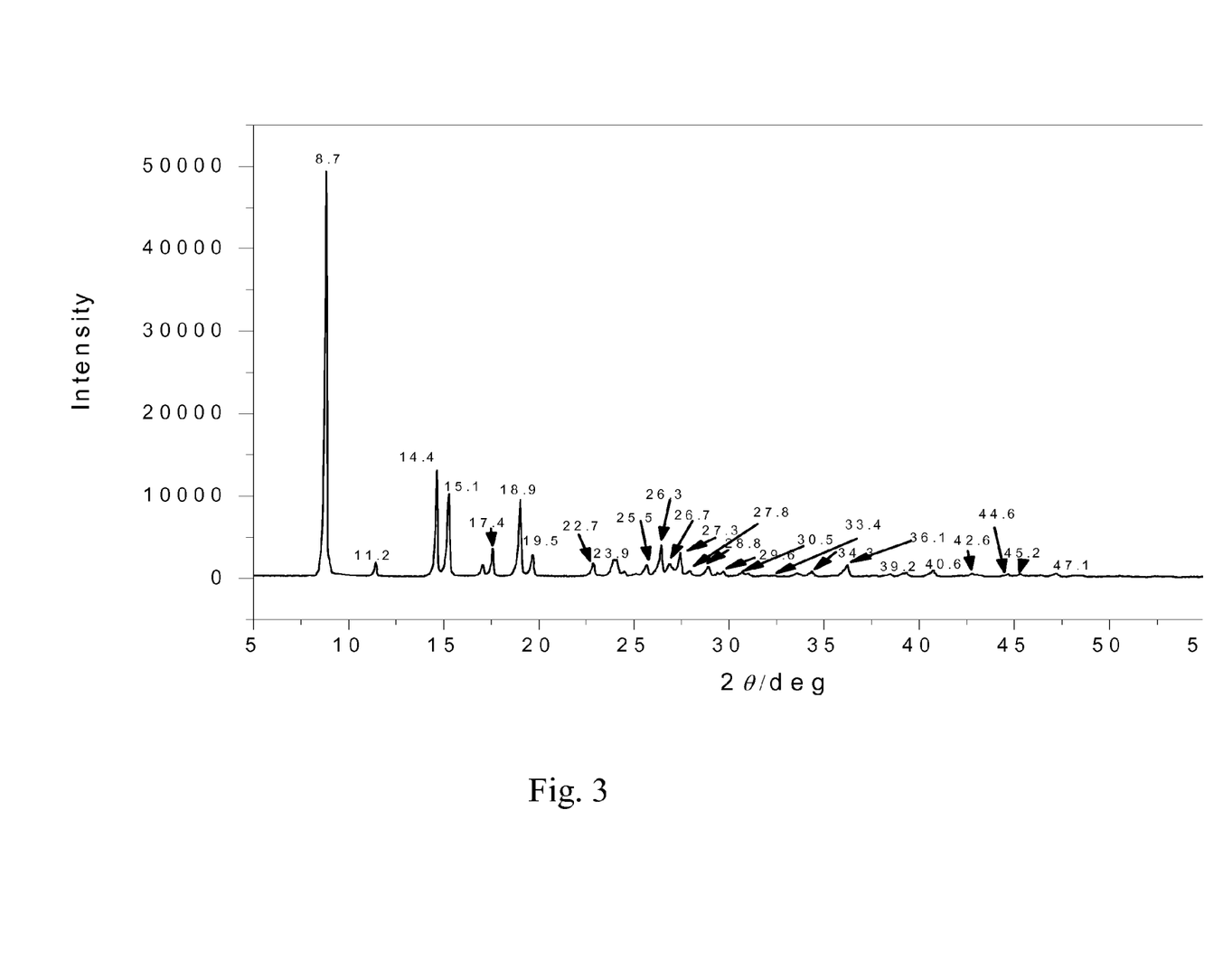
FIG. 3 depicts the X-ray powder diffractogram of the crystalline FFD of the invention.

The physical properties of the crystalline FFD were tested as follows:

using Cu-Ka radiation, its X-ray diffraction pattern is shown in FIG. 3 comprising peaks expressed in degrees $2\theta$ at 8.7, 11.2, 14.4, 15.1, 17.4, 18.9, 19.5, 22.7, 23.9, 25.5, 26.3, 26.7, 27.3, 27.8, 28.8, 29.6, 30.5, 33.4, 34.3, 36.1, 39.2, 40.6, 42.6, 44.6, 45.2, 47.1.

The differential scanning calorimetry (DSC) curve of the crystalline FFD of the invention is shown in FIG. 4 and its endothermic transition temperature was 135.2° C.

The single-crystal X-ray diffraction pattern of the crystalline FFD was analyzed as below:

diffraction experiments were performed on a Bruker Smart 1000 CCD single crystal X-ray diffractometer with graphite monochromator at 150 (2) K. MoKα radiation (0.071073 nm) was used and data were collected by ω/2θ scan mode. The data were processed with the SAINT+ program package and were corrected for absorption effects by using the SADABS program. The space group was determined by the system extinction rule and confirmed by refinement results. All crystal structures were solved with direct methods using full matrix least squares refinement of the SHELXL-97 program. Hydrogen atoms were placed in theoretical calculated positions.

Its unit cell belongs to a monoclinic system and has a space group of $P2_1/n$, wherein a=3.8512(2), b=20.2535(12), c=12.1628(6) Å, β=92.850(5)°, and crystal cell volume V=947.53(9) Å$^3$. Its X-ray single-crystal structure is shown in FIG. 1 and the unit cell is shown in FIG. 2.

Table 1 shows the data obtained from the study.

TABLE 1

Part of the atom coordinates and atomic displacements parameters (U(eq)) of the crystalline FFD.

| Atom | x | y | z | U(eq) |
|---|---|---|---|---|
| C(1) | 10289(7) | 1431(2) | 7417(2) | 26(1) |
| C(2) | 10182(8) | 767(2) | 7200(3) | 30(1) |
| C(3) | 8754(8) | 500(2) | 6240(3) | 31(1) |
| C(4) | 7318(8) | 928(2) | 5455(3) | 30(1) |
| C(5) | 7313(8) | 1607(2) | 5642(2) | 28(1) |
| C(6) | 8774(7) | 1856(2) | 6624(2) | 22(1) |
| C(7) | 7588(7) | 2808(2) | 7791(2) | 25(1) |
| C(8) | 7682(8) | 3508(2) | 7862(2) | 26(1) |
| C(9) | 8845(8) | 3901(2) | 7051(2) | 26(1) |
| C(10) | 10053(7) | 3620(2) | 6072(2) | 24(1) |
| C(11) | 9971(7) | 2959(2) | 5981(2) | 23(1) |
| C(12) | 11350(8) | 4050(2) | 5165(3) | 31(1) |
| F(1) | 11564(5) | 342(1) | 7942(2) | 54(1) |
| N(1) | 8813(6) | 2553(1) | 6808(2) | 22(1) |
| O(1) | 6513(5) | 2441(1) | 8506(2) | 35(1) |
| H(1A) | 11354 | 1596 | 8082 | 31 |
| H(3A) | 8756 | 36 | 6120 | 37 |
| H(4A) | 6326 | 757 | 4783 | 36 |
| H(5A) | 6316 | 1898 | 5100 | 33 |
| H(8A) | 6894 | 3712 | 8507 | 32 |
| H(9A) | 8849 | 4367 | 7140 | 32 |
| H(11A) | 10734 | 2762 | 5326 | 28 |
| H(12A) | 12091 | 3771 | 4562 | 46 |
| H(12B) | 13324 | 4315 | 5453 | 46 |
| H(12C) | 9478 | 4344 | 4893 | 46 |

(The numerals in parentheses are the standard deviations of the last significant digits.)

Example 2

FFD white powder (0.4 g) was added to 10 mL ethanol in a 25 mL test tube. The powder was dissolved with heating and stirring, and then was cooled down. A transparent and clear solution was obtained. After the evaporation of ethanol while standing at room temperature for about one week, a white needle shaped crystal (0.36 g) was formed. The purity (HPLC) was 99.3% and the yield was 90%.

By measurement, the crystalline FFD obtained in this example was a white needle shaped crystal containing no water or other solvents of crystallization. Its unit cell belongs to a monoclinic system and has a space group of $P2_1/n$, wherein a=3.8512(2), b=20.2535(12), c=12.1628(6) Å, β=92.850(5)°, crystal cell volume V=947.53(9) Å$^3$.

Example 3

FFD white powder (0.4 g) was added to 10 mL acetone in a 25 mL test tube. The powder was dissolved with heating and stirring, and then was cooled down. A transparent and clear solution was obtained. After the evaporation of acetone while standing at room temperature for about one week, a white needle shaped crystal (0.32 g) was formed. The purity (HPLC) was 98.6% and the yield was 85%.

By measurement, the crystalline FFD obtained in this example is a white needle shaped crystal containing no water or other crystallization solvents. Its unit cell belongs to a monoclinic system and has a space group of $P2_1/n$, wherein a=3.8512(2), b=20.2535(12), c=12.1628(6) Å, β=92.850(5)° and crystal cell volume V=947.53(9) Å$^3$.

Example 4

The crystalline FFD solid dispersion in this example comprised the crystalline FFD, poloxamer, glycol and polymer base material PEG4000, wherein their ratio by weight was 1:0.2:0.2:5.

The preparation method was the melting method: PEG4000 was first heated to a melt at 90° C. Then the crystalline FFD, poloxamer and glycol were mixed and added into PEG4000. And then the mixture was solidified by rapid cooling in 20 minutes to 35° C. Finally the mixture was freeze-dried into a powder.

Solubility measurement: excess crystalline FFD solid dispersion was put into a cone-shaped bottle with a stopper. After 100 ml purified water was added, the solution was shaken at a constant of 25° C. and 37° C. separately for 48 hours. The filtered supernatants were diluted and their concentrations were measured thrice for each sample. After measurement, the solubility of the crystalline FFD solid dispersion was 52.2±1.56 mg/ml at 25° C. and 64.1±1.77 mg/ml at 37° C. The water solubility of crude crystalline FFD measured with the same method was 2.44~2.55 mg/ml (25° C.) and 3.14~3.16 mg/ml (37° C.).

Example 5

The preparation method was the same as Example 4 except that the crystalline FFD solid dispersion comprised the crystalline FFD, tween-80 and PVP10000, wherein their ratio by weight was 1:0.1:4.

The method for solubility measurement was the same as Example 4. The solubility of the crystalline FFD solid dispersion was 54.3±1.68 mg/ml at 25° C. and 78.6±1.64 mg/ml at 37° C.

Example 6

The preparation method was the same as Example 4 except that the crystalline FFD solid dispersion comprised the crystalline FFD, polyoxyethylene castor oil, glycerol and xanthan gum, wherein their ratio by weight was 1:0.5:0.5:10.

The method for solubility measurement was the same as Example 4. The solubility of the crystalline FFD solid dispersion was 48.9±1.88 mg/ml at 25° C. and 62.0±1.81 mg/ml at 37° C.

Example 7

The crystalline FFD solid dispersion in this example comprised the crystalline FFD, lecithin and PEG12000, wherein their ratio by weight was 1:0.3:7.

The preparation method was the solvent method: the crystalline FFD, lecithin and PEG12000 were added into ethanol, and then ethanol was evaporated at 60° C. using a rotary evaporator.

The method for solubility measurement was the same as Example 4. The solubility of the crystalline FFD solid dispersion was 49.9±1.58 mg/ml at 25° C. and 63.2±1.78 mg/ml at 37° C.

Example 8

The crystalline FFD solid dispersion in this example comprised the crystalline FFD, tween-40 and PEG600, wherein their ratio by weight was 1:0.4:7.

The preparation method was the surface dispersion method: the crystalline FFD was blended with tween-40 and PEG600 and then the mixture was then broken into a powder.

The method for determining the solubility was the same as Example 4. The solubility of the crystalline FFD solid dispersion was 49.1±1.66 mg/ml at 25° C. and 62.3±1.73 mg/ml at 37° C.

Example 9

The crystalline FFD solid dispersion in this example comprised the crystalline FFD, lithium polyethylene glycol 12-hydroxystearate and poloxamer 188, wherein their ratio by weight was 1:0.1:4.

The preparation method was the solvent-melt method: the crystalline FFD was first dissolved in a small amount of acetone, and then added into melting poloxamer 188 at 53° C. The mixture was evaporated with a rotary evaporator at 60° C. for 0.5 hours and then quickly poured onto a −20° C. stainless steel board which was frozen in advance and cooled for 0.5 hours. It was taken out and dried in vacuum for 24 hours at room temperature.

The method for solubility measurement was the same as Example 4. The solubility of the crystalline FFD solid dispersion was 52.6±1.93 mg/ml at 25° C. and 76.5±1.78 mg/ml at 37° C.

Example 10

25 mg Flurofenidone capsules were prepared from the crystalline FFD solid dispersion of Example 4. The ingredients were as follows.

| Ingredients | Percentage % (wt./wt.) | wt./per capsule |
|---|---|---|
| Crystalline FFD solid dispersion | 12.50 | 25 mg |
| Microcrystalline cellulose | 40.00 | 80 mg |
| Lactose | 30.00 | 60 mg |
| Povidone | 4.00 | 8 mg |
| Low-substituted hydroxypropyl cellulose | 10.00 | 20.0 mg |
| Magnesium stearate | 0.90 | 1.8 mg |
| Silica | 2.0 | 4.0 mg |
| Purified water | Remaining amount | Remaining amount |
| total | 100.00 | 200.00 mg |

The process of preparing the capsule was as follows:

1. Preparing adhesive: the prescription amount of povidone was added into purified water, then stirred to dissolve while heating.

2. Mixing: the prescription amounts of the crystalline FFD solid dispersion, microcrystalline cellulose, lactose and low-substituted hydroxypropyl cellulose were sieved separately and mixed uniformly by the method of geometric dilution.

3. Granulating: the prepared adhesive was added and stirred into soft material, wet granules were prepared by using a 20 mesh sieve.

4. Drying and granulating: the prepared wet granules were dried under 55° C. for about 3.5 hours and the granules were prepared by using a 18 mesh sieve.

5. Total mixing: remaining excipients were added into the dry granules and then mixed uniformly.

6. Split charging: a 200 mg quantity was packed into each capsule.

Example 11

The preparation process of 50 mg Flurofenidone capsules was the same as Example 10 except for the ingredients as follows.

| Ingredients | Percentage % (wt./wt.) | wt./per capsule |
|---|---|---|
| Crystalline FFD solid dispersion | 25.00 | 50 mg |
| Pregelatine starch | 28.00 | 56 mg |
| Lactose | 30.00 | 60 mg |
| Povidone | 4.00 | 8 mg |
| Crosslinking povidone | 10.00 | 20.0 mg |
| Silica | 1.50 | 3.00 mg |
| Purified water | Remaining amount | Remaining amount |
| Total | 100.00 | 200.00 mg |

Example 12

The preparation process of 100 mg Flurofenidone capsules was the same as Example 10 except for the ingredients as follows.

| Ingredients | Percentage % (wt./wt.) | wt./per capsule |
|---|---|---|
| Crystalline FFD solid dispersion | 50.00 | 100 mg |
| Microcrystalline cellulose | 10.00 | 20 mg |
| Lactose | 20.00 | 40 mg |
| Povidone | 5.00 | 10 mg |
| Crosslinking povidone | 6.00 | 12 mg |
| Low substituted hydroxypropyl cellulose | 8.00 | 16 mg |
| Talcum powder | 0.9 | 1.8 mg |
| Purified water | Remaining amount | Remaining amount |
| Total | 100.00 | 200.00 mg |

Example 13

25 mg Flurofenidone tablets were prepared from the crystalline FFD solid dispersion of Example 5, the ingredients were as follows.

| Ingredients | Percentage % (wt./wt.) | wt./per tablet |
| --- | --- | --- |
| Crystalline FFD solid dispersion | 75.00 | 150 mg |
| Microcrystalline cellulose | 10.00 | 20 mg |
| Lactose | 10.00 | 20 mg |
| Povidone | 3.00 | 6 mg |
| Low-substituted hydroxypropyl cellulose | 1.50 | 3 mg |
| Magnesium stearate | 0.5 | 1 mg |
| Purified water | Remaining amount | Remaining amount |
| Total | 100.00 | 200.00 mg |

The process of preparing Flurofenidone tablets in this example was as follows:

1. Preparing adhesive: the prescription amount of povidone was added into purified water and stirred to dissolve while heating.
2. Mixing: the prescription amount of crystalline FFD solid dispersion, microcrystalline cellulose, lactose and low-substituted hydroxypropyl cellulose were sieved separately and then mixed uniformly by the method of geometric dilution.
3. Granulating: the prepared adhesive was added and stirred into soft material, wet granules were prepared by using a 20 mesh sieve.
4. Drying and granulating: the prepared wet granules were dried under 55° C. for about 3 hours, the granules were prepared by using a 18 mesh sieve.
5. Total mixing: remaining excipients were added into dry granules and mixed uniformly. The amount of semi-final product was determined.
6. Tableting: tableting in 200 mg per tablet.

Example 14

The preparation process of 100 mg Flurofenidone tablets was the same as Example 13 except for the ingredients as follows.

| Ingredients | Percentage % (wt./wt.) | wt./per tablet |
| --- | --- | --- |
| Crystalline FFD solid dispersion | 50.00 | 100 mg |
| Pregelatin starch | 20.00 | 40 mg |
| Lactose | 25.00 | 50 mg |
| Povidone | 3.00 | 6 mg |
| Low substituted hydroxypropyl cellulose | 1.50 | 3 mg |
| Magnesium stearate | 0.5 | 1 mg |
| Purified water | Remaining amount | Remaining amount |
| Total | 100.00 | 200.00 mg |

Example 15

The preparation process of 450 mg Flurofenidone tablets was the same as Example 13 except for the ingredients as follows.

| Ingredients | Percentage % (wt./wt.) | wt./per tablet |
| --- | --- | --- |
| Crystalline FFD solid dispersion | 25.00 | 50 mg |
| Microcrystalline cellulose | 30.00 | 60 mg |
| Lactose | 15.00 | 30 mg |
| Povidone | 3.00 | 6 mg |
| Low substituted hydroxypropyl cellulose | 1.50 | 3 mg |
| Talcum powder | 0.5 | 1 mg |
| Purified water | Remaining amount | Remaining amount |
| Total | 100.00 | 200.00 mg |

Example 16

150 mg Flurofenidone granules were prepared from the crystalline FFD solid dispersion of Example 5, the ingredients were as follows.

| Ingredients | Percentage % (wt./wt.) | wt./per bag |
| --- | --- | --- |
| Crystalline FFD solid dispersion | 15.00 | 150 mg |
| Sucrose | 66.00 | 660 mg |
| Sucrose pulp by 10% sucrose content | 10.00 | 100 mg |
| Low substituted hydroxypropyl cellulose | 6.00 | 60 mg |
| Poloxamer | 2.50 | 25 mg |
| Sodium benzoate | 0.5 | 5 mg |
| Purified water | Remaining amount | Remaining amount |
| Total | 100.00 | 1000.00 mg |

The preparation process of Flurofenidone granules in this example was as follows:

1. Preparing adhesive: the prescription amount of sucrose was added into purified water and was stirred while heating to obtain 10% sugar syrup.
2. Mixing: the prescription amounts of the crystalline FFD solid dispersion, sucrose and low substituted hydroxypropyl cellulose were sieved separately and then were mixed uniformly by process of geometric dilution.
3. Granulating: the prepared adhesive was added and stirred into soft material, wet granules were prepared by using a 20 mesh sieve.
4. Drying and granulating: the prepared wet granules were dried under 55° C. for about 4 hours which was sieved by using a 12 mesh to 40 mesh sieve.
5. Total mixing: remaining excipients were added into dry granules and mixed uniformly. The amount of semi-final product was determined.
6. Split charging: Split charging with lightproof complex film in 1 g per bag.

Example 17

The preparation process of 100 mg Flurofenidone granules was the same as Example 16 except for the ingredients as follows.

| Ingredients | Percentage % (wt./wt.) | wt./per bag |
| --- | --- | --- |
| FFD crystalline solid dispersion | 10.00 | 100 mg |
| Sucrose | 68.00 | 680 mg |

-continued

| Ingredients | Percentage % (wt./wt.) | wt./per bag |
|---|---|---|
| Sucrose pulp by 10% sucrose content | 10.00 | 100 mg |
| Sodium carboxy methyl cellulose | 8.00 | 80 mg |
| Poloxamer | 3.50 | 35 mg |
| Sodium benzoate | 0.5 | 5 mg |
| Purified water | Remaining amount | Remaining amount |
| Total | 100.00 | 1000.00 mg |

Example 18

The preparation process of 50 mg Flurofenidone tablets was the same as Example 16 except for the ingredients as follows.

| Ingredients | Percentage % (wt./wt.) | wt./per bag |
|---|---|---|
| FFD crystalline solid dispersion | 5.00 | 50 mg |
| Sucrose | 72.00 | 720 mg |
| Sucrose pulp by 10% sucrose content | 10.00 | 100 mg |
| Sodium carboxy methyl cellulose | 8.00 | 80 mg |
| Poloxamer | 4.20 | 42 mg |
| Sodium benzoate | 0.80 | 8 mg |
| Purified water | Remaining amount | Remaining amount |
| Total | 100.00 | 1000.00 mg |

Example 19

A 150 mg Flurofenidone suspension was prepared from the crystalline FFD solid dispersion of Example 6, the ingredients were as follows.

| Ingredients | Percentage % (wt./wt.) | wt./per bottle |
|---|---|---|
| Crystalline FFD solid dispersion | 15.00 | 1500 mg |
| CMC-Na | 1.00 | 100 mg |
| Tragacanth | 0.50 | 50 mg |
| Tween-80 | 1.00 | 100 mg |
| Steviol glycosides | 0.10 | 10 mg |
| Sodium benzoate | 0.50 | 50 mg |
| Purified water | 81.90 | 8190 mg |
| Total | 100.00 | 10000 mg |

The method of preparation was as follows:
the prescription amounts of CMC-Na and tragacanth were added into 1000 mg purified water and swelled overnight to obtain liquid A.
The prescription amount of the crystalline FFD was wetted with the prescription amount of tween-80. A small amount of water and the liquid A were added and mixed fully. Then the prescription amount of sodium benzoate and steviol glycosides were added into the mixture and following by adding purified water until the total weight was 10000 mg. Flurofenidone suspension was obtained after sterilizing and filling into the bottle.

Example 20

The preparation process of a 100 mg Flurofenidone suspension was the same as Example 19 except for the ingredients as follows.

| Ingredients | Percentage % (wt./wt.) | wt./per bottle |
|---|---|---|
| Crystalline FFD solid dispersion | 10.00 | 1000 mg |
| CMC-Na | 0.80 | 80 mg |
| Tragacanth | 0.50 | 50 mg |
| Tween-80 | 0.80 | 80 mg |
| Steviol glycosides | 0.10 | 10 mg |
| Sodium benzoate | 0.50 | 50 mg |
| Purified water | 87.30 | 8730 mg |
| Total | 100.00 | 10000 mg |

Example 21

The preparation process of a 50 mg Flurofenidone suspension was the same as Example 19 except for the ingredients as follows.

| Ingredients | Percentage % (wt./wt.) | wt./per bottle |
|---|---|---|
| Crystalline FFD solid dispersion | 10.00 | 1000 mg |
| CMC-Na | 0.60 | 60 mg |
| Tragacanth | 0.50 | 50 mg |
| Tween-80 | 0.60 | 60 mg |
| Steviol glycosides | 0.10 | 10 mg |
| Sodium benzoate | 0.50 | 50 mg |
| Purified water | 87.70 | 8770 mg |
| Total | 100.00 | 10000 mg |

Example 22

A 150 mg Flurofenidone emulsion was prepared from the crystalline FFD solid dispersion of Example 7, the ingredients were as follows.

| Ingredients | Percentage % (wt./wt.) | wt./per bottle |
|---|---|---|
| Crystalline FFD solid dispersion | 15.00 | 1500 mg |
| Soybean oil | 15.00 | 1500 mg |
| Caprylic/capric glyceride | 15.00 | 1500 mg |
| Phospolipid | 6.00 | 600 mg |
| Tragacanth | 0.20 | 20 mg |
| Glycerol | 4.00 | 400 mg |
| Glycol | 4.00 | 400 mg |
| Organic silicon | 0.60 | 60 mg |
| Purified water | 40.20 | 4020 mg |
| Total | 100.00 | 10000 mg |

The method of preparation was as follows:
The prescription amount of tragacanth was added into 1000 mg purified water and swelled overnight.
The prescription amount of the crystalline FFD, soybean oil, caprylic/capric glyceride and phospholipid were mixed and heated to 60° C. It was prepared as the oil phase.
The prescription amount of glycerol, glycol, tragacanth solution and organic silicon were added into water successively and stirred until completely dissolved to a uniform liquid. It was prepared as the water phase.

The oil phase was first stirred under a high shear dispersing emulsifier, then the water phase was added slowly. The speed was controlled at 10,000 RPM. The mixture was sheared for 10 minutes to form a milky opaque liquid which was the Flurofenidone emulsion.

Example 23

The ingredients of a 100 mg Flurofenidone emulsion were as follows:

| Ingredients | Percentage % (wt./wt.) | wt./per bottle |
|---|---|---|
| Crystalline FFD solid dispersion | 10.00 | 1000 mg |
| Soybean oil | 10.00 | 1000 mg |
| Caprylic/capric glyceride | 12.00 | 1200 mg |
| Phospholipid | 4.00 | 400 mg |
| Tragacanth | 0.20 | 20 mg |
| Glycerol | 4.00 | 400 mg |
| Glycol | 4.00 | 400 mg |
| Organic silicon | 0.60 | 60 mg |
| Purified water | 55.20 | 5520 mg |
| Total | 100.00 | 10000 mg |

The method of preparation was as follows:

The prescription amount of tragacanth was added into 1000 mg purified water and swelled overnight.

The prescription amount of the crystalline FFD, soybean oil, caprylic/capric glyceride and phospholipid were mixed and heated to 60° C. It was prepared as the oil phase.

The prescription amount of glycerol, glycol, tragacanth solution, organic silicon were added into water successively while stirring. The mixture was stirred until completely dissolved to a uniform liquid. It was prepared as the water phase.

The oil phase was first stirred under a high shear dispersing emulsifier, then the water phase was added slowly and the speed was controlled at 10,000 RPM. The mixture was sheared for 8 minutes to form a milky opaque liquid, which was the Flurofenidone emulsion.

Example 24

The ingredients of a 50 mg Flurofenidone emulsion were as follows:

| Ingredients | Percentage % (wt./wt.) | wt./per bottle |
|---|---|---|
| Crystalline FFD solid dispersion | 5.00 | 500 mg |
| Soybean oil | 5.00 | 1000 mg |
| Caprylic/capric glyceride | 10.00 | 1000 mg |
| Phospolipid | 3.00 | 300 mg |
| Tragacanth | 0.20 | 20 mg |
| Glycerol | 4.00 | 400 mg |
| Glycol | 4.00 | 400 mg |
| Organic silicon | 0.60 | 60 mg |
| Purified water | 68.20 | 6820 mg |
| Total | 100.00 | 10000 mg |

The method of preparation was as follows:

The prescription amount of tragacanth was added into 1000 mg purified water and swelled overnight.

The prescription amount of the crystalline FFD, soybean oil, caprylic/capric glyceride and phospholipid were mixed and heated to 60° C. It was prepared as an oil phase.

The prescription amount of glycerol, glycol, tragacanth solution, organic silicon were added into the water successively with stirring. The mixture was stirred until completely dissolved to a uniform liquid. It was prepared as the water phase.

The oil phase was first stirred under a high shear dispersing emulsifier, then the water phase was added slowly and the speed was controlled at 10,000 RPM. The mixture was sheared for 8 minutes to form a milky opaque liquid which was the Flurofenidone emulsion.

Example 25

A 150 mg semi-solid Flurofenidone was prepared from the crystalline FFD solid dispersion in Example 8, the ingredients were as follows.

| Ingredients | Percentage % (wt./wt.) | wt./per bottle |
|---|---|---|
| Crystalline FFD solid dispersion | 15.00 | 1500 mg |
| Vaseline | 10.00 | 1000 mg |
| Lanolin | 15.00 | 1500 mg |
| Carbomer | 10.00 | 1000 mg |
| PEG4000 | 15.00 | 1500 mg |
| Purified water | 45.00 | 4500 mg |
| Total | 100.00 | 10000.00 mg |

The method of preparation was as follows:

The crystalline FFD was shattered into powder and sieved; the prescription amount of Vaseline was added and mixed uniformly to obtain mixture A.

The prescription amount of lanolin, carbomer, PEG4000 and water were mixed fully to obtain mixture B.

The mixture A and B were mixed uniformly, sterilized and filled into the bottle to obtain semi-solid Flurofenidone.

Example 26

The preparation process was the same as Example 25 except for the ingredients of a 100 mg Flurofenidone semi-solid preparation as follows.

| Ingredients | Percentage % (wt./wt.) | wt./per bottle |
|---|---|---|
| Crystalline FFD solid dispersion | 10.00 | 1000 mg |
| Vaseline | 10.00 | 1000 mg |
| Lanolin | 15.00 | 1500 mg |
| Carbomer | 10.00 | 1000 mg |
| PEG4000 | 15.00 | 1500 mg |
| Purified water | 50.00 | 5000 mg |
| Total | 100.00 | 10000.00 mg |

Example 27

The preparation process of a 50 mg semi-solid Flurofenidone was the same as Example 25 except for the ingredients as follows.

| Ingredients | Percentage % (wt./wt.) | wt./per bottle |
|---|---|---|
| Crystalline FFD solid dispersion | 5.00 | 500 mg |
| Vaseline | 10.00 | 1000 mg |
| Lanolin | 15.00 | 1500 mg |
| Carbomer | 10.00 | 1000 mg |
| PEG4000 | 15.00 | 1500 mg |
| Purified water | 55.00 | 5500 mg |
| Total | 100.00 | 10000.00 mg |

Although the present invention has been described in detail by way of illustration and example, it will be readily apparent to those of ordinary skill in the art in light of the teachings of this invention that certain changes and modifications may be made thereto without departing from the spirit or scope of the appended claims.

INDUSTRIAL PRACTICABILITY

The present invention provides a crystalline pyridone compound, which is a white needle shaped crystal containing no water or other crystallization solvents. Its unit cell belongs to a monoclinic system and has a space group of $P2_1/n$, wherein a=3.8512(2), b=20.2535(12), c=12.1628(6) Å, β=92.850(5)° and crystal cell volume V=947.53(9) Å³.

The crystalline FFD of the invention has the needed properties for preparing or making treatment compositions in large scale. The crystalline FFD also has a good melting point, good flowability and bulk density, therefore it is easier to prepare and manufacture the compositions containing the crystalline FFD. The present invention can eliminate or minimize by-products produced during the synthesis process of making FFD, wherein the purity is at least about 98% (w/w). It can be used for treating organs fibrosis of liver, kidney, lung and the like and for reducing skin scars.

What is claimed is:

1. A crystalline 1-(3-fluorophenyl)-5-methyl-2-(1H)-pyridone, that is characterized by being a white needle shape crystal containing no water or a solvent of crystallization, and having crystal in monoclinic space group $P2_1/n$ with unit cell parameters: a=3.8512(2), b=20.2535(12), c=12.1628(6) Å, p=92.850 (5)°, and cell volume V=947.53(9) Å³.

2. A crystalline 1-(3-fluorophenyl)-5-methyl-2-(1H)-pyridone, characterized by an X-ray diffraction pattern comprising peaks expressed in degrees 2θ at 8.7, 11.2, 14.4, 15.1, 17.4, 18.9, 19.5, 22.7, 23.9, 25.5, 26.3, 27.3, 36.1 and 39.2.

3. The crystalline 1-(3-fluorophenyl)-5-methyl-2-(1H)-pyridone of claim 1, characterized in that its endothermic transition temperature is 135.2° C.

4. A method of preparing the crystalline 1-(3-fluorophenyl)-5-methyl-2-(1H)-pyridone of claim 1, characterized by (1) dissolving 1-(3-fluorophenyl)-5-methyl-2-(1H)-pyridone in an organic solvent first, and (2) forming the crystalline 1-(3-fluorophenyl)-5-methyl-2-(1H)-pyridone after evaporating the organic solvent while standing at room temperature.

5. The method of preparing the crystalline 1-(3-fluorophenyl)-5-methyl-2-(1H)-pyridone according to claim 4, wherein the organic solvent is ethyl acetate, methanol, ethanol or acetone.

6. A crystalline 1-(3-fluorophenyl)-5-methyl-2-(1H)-pyridone solid dispersion, characterized by comprising the crystalline 1-(3-fluorophenyl)-5-methyl-2-(1H)-pyridone of claim 1, a solubilizer and a polymer base material, wherein their ratio by weight is 1 to 0.1-0.5 to 4-10.

7. The crystalline 1-(3-fluorophenyl)-5-methyl-2-(1H)-pyridone solid dispersion of claim 6, characterized by further comprising a cosolvent, which is present in an amount from 0.1 to 0.5 times by weight relative to the weight of the crystalline 1-(3-fluorophenyl)-5-methyl-2-(1H)-pyridone.

8. The crystalline 1-(3-fluorophenyl)-5-methyl-2-(1H)-pyridone solid dispersion of claim 6, wherein the solubilizer is sodium dodecyl sulphate, vitamin C, tween-20, tween-21, tween-40, tween-60, tween-61, tween-65, tween-80, tween-81, tween-85, tween-120, myrij, brij, poloxamer, caprylic/capric glyceride, lithium polyethylene glycol 12-hydroxystearate, polyoxyethylene stearic acid ester, polyoxyethylene castor oil, polyoxyethylene hydrogenated castor oil or lecithin.

9. The crystalline 1-(3-fluorophenyl)-5-methyl-2-(1H)-pyridone solid dispersion of claim 6, wherein said the polymer base material is PEG4000, PEG6000, yellow gum, PEG12000, PEG20000, PVPK90, PVP10000, PVP40000 or poloxamer 188.

10. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone of claim 1 to the patient.

11. The crystalline 1-(3-fluorophenyl)-5-methyl-2-(1H)-pyridone of claim 2, characterized by an X-ray diffraction pattern comprising peaks expressed in degrees 2θ at 8.7, 11.2, 14.4, 15.1, 17.4, 18.9, 19.5, 22.7, 23.9, 25.5, 26.3, 26.7, 27.3, 27.8, 28.8, 29.6, 30.5, 33.4, 34.3, 36.1, 39.2, 40.6, 42.6, 44.6, 45.2 and 47.1.

12. The crystalline 1-(3-fluorophenyl)-5-methyl-2-(1H)-pyridone of claim 1, characterized in that its endothermic transition temperature is from 132.5° C. to 136.0° C.

13. The crystalline 1-(3-fluorophenyl)-5-methyl-2-(1H)-pyridone of claim 2, characterized in that its endothermic transition temperature is from 132.5° C. to 136.0° C.

14. The crystalline 1-(3-fluorophenyl)-5-methyl-2-(1H)-pyridone of claim 11, characterized in that its endothermic transition temperature is from 132.5° C. to 136.0° C.

15. A method of preparing the crystalline 1-(3-fluorophenyl)-5-methyl-2-(1H)-pyridone of claim 2, characterized by dissolving 1-(3-fluorophenyl)-5-methyl-2-(1H)-pyridone in an organic solvent first, and forming the crystalline 1-(3-fluorophenyl)-5-methyl-2-(1H)-pyridone after evaporating the organic solvent while standing at room temperature.

16. A crystalline 1-(3-fluorophenyl)-5-methyl-2-(1H)-pyridone solid dispersion, characterized by comprising the crystalline 1-(3-fluorophenyl)-5-methyl-2-(1H)-pyridone of claim 2, a solubilizer and a polymer base material, wherein their ratio by weight is 1 to 0.1-0.5 to 4-10.

17. The crystalline 1-(3-fluorophenyl)-5-methyl-2-(1H)-pyridone solid dispersion of claim 16, characterized by further comprising a cosolvent, which is present in an amount from 0.1 to 0.5 times by weight relative to the weight of the crystalline 1-(3-fluorophenyl)-5-methyl-2-(1H)-pyridone.

18. A method of preparing the crystalline 1-(3-fluorophenyl)-5-methyl-2-(1H)-pyridone of claim 11, characterized by dissolving 1-(3-fluorophenyl)-5-methyl-2-(1H)-pyridone in an organic solvent first, and forming the crystalline 1-(3-fluorophenyl)-5-methyl-2-(1H)-pyridone after evaporating the organic solvent while standing at room temperature.

19. A crystalline 1-(3-fluorophenyl)-5-methyl-2-(1H)-pyridone solid dispersion, characterized by comprising the crystalline 1-(3-fluorophenyl)-5-methyl-2-(1H)-pyridone of claim 11, a solubilizer and a polymer base material, wherein their ratio by weight is 1 to 0.1-0.5 to 4-10.

20. The crystalline 1-(3-fluorophenyl)-5-methyl-2-(1H)-pyridone solid dispersion of claim 19, characterized by further comprising a cosolvent, which is present in an amount from 0.1 to 0.5 times by weight relative to the weight of the crystalline 1-(3-fluorophenyl)-5-methyl-2-(1H)-pyridone.

21. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone of claim 2 to the patient.

22. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone of claim 11 to the patient.

23. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone solid dispersion of claim 6 to the patient.

24. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone solid dispersion of claim 16 to the patient.

25. A method for treating hepatic fibrosis, renal fibrosis, pulmonary fibrosis and other organs fibrosis or for reducing skin scar in a patient by administering the crystalline 1-(3-fluorophenyl)-5-methyl-2-(1H)-pyridone solid dispersion of claim 19 to the patient.

\* \* \* \* \*